United States Patent [19]

Platz et al.

[11] 4,258,203

[45] Mar. 24, 1981

[54] PREPARATION OF BUTANEDICARBOXYLIC ACID ESTERS

[75] Inventors: Rolf Platz, Mannheim; Rudolf Kummer, Frankenthal; Heinz-Walter Schneider, Ludwigshafen, all of Fed. Rep. of Germany

[73] Assignee: BASF Aktiengesellschaft, Fed. Rep. of Germany

[21] Appl. No.: 58,944

[22] Filed: Jul. 19, 1979

[30] Foreign Application Priority Data

Aug. 21, 1978 [DE] Fed. Rep. of Germany ....... 2836518

[51] Int. Cl.$^3$ .............................................. C07C 67/38
[52] U.S. Cl. .................................................. 560/204
[58] Field of Search ........................................ 560/204

[56] References Cited

U.S. PATENT DOCUMENTS

| 3,778,466 | 12/1973 | Matsuda | 560/204 |
| 4,169,956 | 10/1979 | Kummer et al. | 560/204 |

OTHER PUBLICATIONS

Matsuda, Bull. Chem. Soc. Japan, vol. 46 (1973), 524–530.

*Primary Examiner*—Bernard Helfin
*Attorney, Agent, or Firm*—Keil & Witherspoon

[57] ABSTRACT

Multistep process for the preparation of butanedicarboxylic acid by the hydrogenation of carbon monoxide under pressure in the presence of a cobalt carbonyl catalyst, the improvement of heating at a temperature of 250° to 350° C. under superatmospheric pressure the resulting aqueous solution of cobalt carbonyl hydride that has been extracted with butadiene or with mixtures thereof before using in a subsequent step of the multistep process.

6 Claims, No Drawings

PREPARATION OF BUTANEDICARBOXYLIC ACID ESTERS

The present invention relates to a process for the preparation of butanedicarboxylic acid esters, in which butadiene or a hydrocarbon mixture containing butadiene is reacted with carbon monoxide and a lower alkanol in the presence of a tertiary nitrogen base and of cobalt carbonyl at from 80° to 150° C. under superatmospheric pressure and the resulting pentenoic acid ester is further reacted with carbon monoxide and a lower alkanol at from 140° to 200° C. under superatmospheric pressure to give a butanedicarboxylic acid ester, the cobalt-containing catalyst solution being recylced.

Bull. Chem. Soc. Japan 46 (1973), 524 et seq., discloses a two-stage process for the preparation of adipic acid esters from butadiene, wherein butadiene is first reacted with carbon monoxide and an alkanol in the presence of cobalt carbonyl and a nitrogen base, eg. pyridine or isoquinoline, and in a subsequent stage, without removing the catalyst, the pentenoic acid ester formed is further reacted with carbon monoxide and an alkanol to give an adipic acid ester. However, in carrying out such a process industrially it is necessary to recover and recycle the catalyst. Thus, in the process disclosed in U.S. Pat. No. 3,778,466, the catalyst-containing residue obtained after distilling off the useful products is reused for the carbonylation. However, it has been found that the activity of the catalyst drops substantially after it has been used, for example, four times.

It has also already been proposed to reuse cobalt salt solutions, recovered from the reaction mixture after a treatment with an oxidizing agent, with or without a treatment of the solutions with an ion exchanger before they are reused. However, it has been found, as a result of the nature of the impurities, that the process requires improvement if the cobalt salt solution is to be recycled several times. The accumulation of dicarboxylic acids and of nitrogen bases, for example conversion products of pyridine, results in materials separating out, and in sparingly soluble oils being formed. This causes part of the cobalt catalyst to separate out, causing pipeline blockages. The compounds which have separated out can only be reconverted with difficulty to catalytically active compounds.

It is an object of the present invention to modify the process so that the cobalt catalyst retains a high catalytic activity even after repeated reuse, that no by-products accumulate and that the difficulties associated with the latter are eliminated.

We have found that this object is achieved in a process for the preparation of butanedicarboxylic acid esters, in which (a) an aqueous cobalt salt solution is treated, at from 50° to 200° C. and under a pressure of from 50 to 500 bar, with excess carbon monoxide and hydrogen in the presence of active charcoal laden with cobalt carbonyl, (b) the resulting aqueous solution of cobalt carbonyl hydride is extracted with butadiene, or with a hydrocarbon mixture containing butadiene, and the aqueous phase is separated off, (c) the butadiene, or the butadiene/hydrocarbon mixture, containing cobalt carbonyl hydride, cobalt carbonyl and butenyl-cobalt tricarbonyl, is reacted with carbon monoxide and a $C_1$–$C_4$-alkanol in excess in the presence of from 0.5 to 2 moles, per mole of butadiene, of a tertiary nitrogen base having a $pK_a$ of from 3 to 11, at from 80° to 150° C. and under a pressure of from 300 to 2,000 bar, (d) the tertiary nitrogen base contained in the resulting reaction mixture is removed until its content reaches 0.1–0.3 mole per mole of pentenoic acid ester, excess hydrocarbons are also removed, the pentenoic acid ester remaining in the reaction mixture is reacted with carbon monoxide and a $C_1$–$C_4$-alkanol in excess at from 140° to 200° C. and under a pressure of from 100 to 400 bar in the presence of the amounts of cobalt carbonyl and tertiary nitrogen base present in the reaction mixture, and excess alkanol and free nitrogen base are then distilled off, and (e) the reaction mixture which is left and which contains a cobalt catalyst, butanedicarboxylic acid ester and by-products is treated with oxidizing agents in the presence of the aqueous acid solution which has been removed in stage (b), and the mixture is separated into an organic phase, from which butanedicarboxylic acid ester is isolated by distillation, and an aqueous phase, containing cobalt salts, which is recycled to stage (a), wherein the aqueous phase separated off in stage (b) is heated at from 250° to 300° C. under superatmospheric pressure before being used in stage (e).

The novel process has the advantage that the catalyst solution can be reused without adverse consequences. In particular, the separating-out of insoluble compounds and the formation of compounds which are difficult to convert to active catalysts are substantially avoided. The novel process has the further advantage that the treatment which it entails is technically simple and does not require any expensive auxiliary means. In addition, the novel process has the advantage that the by-products are converted into products easily removable by distillation and are removed from the system, and that when using pyridine as the nitrogen base a proportion of the undesired compounds is reconverted to pyridine.

In a first stage (stage a), aqueous cobalt salt solutions are treated with carbon monoxide and hydrogen in excess at from 50° to 200° C. under a pressure of from 50 to 500 bar in the presence of active charcoal charged with cobalt carbonyl. Preferred cobalt salts are water-soluble salts of fatty acids, especially formates, acetates, propionates or butyrates. Cobalt formate and cobalt acetate have proved particularly suitable. It is advantageous to start from a solution which contains from 0.5 to 5% by weight of cobalt, calculated as metal, in particular from 1 to 3% by weight of cobalt in the form of the salts mentioned. In general, the gas mixture contains carbon monoxide and hydrogen in a volume ratio of from 4:1 to 1:2, especially from 2:1 to 1:1. An approximately equimolecular mixture of carbon monoxide and hydrogen has proved particularly suitable. Advantageously, the mixture of carbon monoxide and hydrogen is used in excess, for example in up to 5 times the stoichiometrically required amount. It has proved advantageous to maintain a temperature of from 100° to 170° C. and a pressure of from 100 to 400 bar.

The treatment in stage (a) takes place in the presence of active charcoal. Examples of suitable types of active charcoal are peat charcoal, animal charcoal and sugar charcoal, the first-mentioned having proved particularly suitable. Advantageously, the active charcoal is charged with cobalt carbonyl to the saturation point. In general, this is achieved by passing an aqueous solution of a cobalt salt together with the stated gas mixture of carbon monoxide and hydrogen over the active charcoal under the stated reaction conditions until the charcoal is saturated, ie. until cobalt carbonyl and cobalt carbonyl hydride are analytically detectable in the material leaving the charcoal.

In general, the treatment is carried out in a treatment zone which advantageously has a length:diameter ratio of from 5:1 to 50:1 and in which the active charcoal is as a rule in the form of a fixed bed. Preferably, the throughput of cobalt is from 1.5 to 15 g, calculated as metal but in the form of one of the salts mentioned, per hour per kilogram of active charcoal.

The aqueous solution obtained, containing cobalt carbonyl hydride, unconverted cobalt salt and liberated acid is advantageously fed to the second stage (stage b) together with the unconsumed mixture of carbon monoxide and hydrogen, preferably without releasing the pressure. In the second stage, cobalt carbonyl hydride is extracted by means of butadiene or butadiene-containing hydrocarbon mixtures which will be discussed in more detail below. The extraction may be carried out with all or only a part of the butadiene required for the carbonylation. Advantageously, from 5 to 30 moles of butadiene are used per gram atom of cobalt to be extracted. The extraction is carried out in counter-current or co-current in equipment conventionally used for industrial extractions, for example columns or static mixers. During the extraction, a temperature of from 20° to 100° C. and a pressure of from 5 to 300 bar are maintained. The mixture is subsequently separated into an aqueous phase and an organic phase. If the extraction is, for example, carried out in a pressure tube filled with Raschig rings, a separation into an organic phase and an aqueous phase at the same time occurs in the upper part. At the same time, the mixture of carbon monoxide and hydrogen also employed is separated off as the gas phase. The cobalt content of the organic phase leaving stage (b) is in general from 1 to 5% by weight. We assume that the cobalt carbonyl is present in the organic phase as a water-insoluble complex compound with butadiene.

The aqueous phase separated off still contains up to about 1% by weight of $Co^{2+}$ in the form of the salt employed, and up to 4% by weight of free acid corresponding to the cobalt salt employed.

In stage (c), the organic phase is then reacted with CO and a $C_1$–$C_4$-alkanol in excess, advantageously using from 1.5 to 4 moles per mole of butadiene, in the presence of from 0.5 to 2 moles, per mole of butadiene, of a tertiary nitrogen base having a $pK_a$ of from 3 to 11, with the proviso that the tertiary nitrogen base should preferably be lower-boiling than the pentenoic acid ester to be prepared, at from 80° to 150° C. under a pressure of from 300 to 2,000 bar.

If less than the total amount of butadiene, or of hydrocarbon mixture containing butadiene, required for the carbonylation has been used for the extraction, the requisite amount of additional starting materials is added in stage (c). It should be noted that instead of pure butadiene, butadiene-containing hydrocarbon mixtures can advantageously be used. Such hydrocarbon mixtures contain, in addition to butadiene, saturated hydrocarbons of 3 to 5 carbon atoms and monoolefinically unsaturated hydrocarbons of 3 to 5 carbon atoms. The butadiene content should as a rule be more than 10% by weight. In industry, $C_4$-cuts, in particular, are used as the starting mixture. Such cuts include any mixture of predominantly linear $C_4$-hydrocarbons which contains more than 10% by weight of 1,3-butadiene (simply referred to as butadiene) and more than 15% by weight of butenes. As a rule, such $C_4$-cuts have the following composition:

Butadiene: 40–60% by weight
Isobutene: 20–35% by weight
But-1-ene: 10–25% by weight
But-2-ene: 5–15% by weight
Butanes: 1–10% by weight
Butynes: 0.1–3% by weight Such $C_4$-cuts are obtained, for example, from the dehydrogenation of butane or butene, or as by-products of the production of ethylene by thermal cracking of light naphtha or of higher hydrocarbon cuts.

Suitable tertiary nitrogen bases are, preferably, N-heterocyclic compounds, eg. pyridine ($pK_a$ 5.3), methylpyridines, eg. 3-picoline ($pK_a$ 6.0), and isoquinoline ($pK_a$ 5.4), as well as trialkylamines, eg. trimethylamine ($pK_a$ 9.8) or triethylamine ($pK_a$ 11.0). Pyridine has acquired particular industrial importance.

It has proved particularly advantageous to use from 0.6 to 1.5 moles of tertiary nitrogen base per mole of butadiene.

Examples of suitable $C_1$–$C_4$-alkanols are methanol, ethanol, propanol, butanol and isobutanol. The use of methanol is particularly preferred.

The reaction is preferably carried out at from 120° to 140° C. under a pressure of from 600 to 1,200 bar. As a rule, from 0.01 to 0.1 gram atom of cobalt, in the form of the cobalt carbonyl complexes described, is used per mole of butadiene.

The reaction mixture obtained contains unconverted butadiene, other hydrocarbons where relevant, tertiary nitrogen base, cobalt carbonyl compounds, unconverted alkanol, the pentenoic acid ester formed as the desired product, and by-products such as valeric acid esters, vinylcyclohexene, butenyl and butyl ketones and butadiene polymers.

After releasing the pressure, the tertiary nitrogen base contained in the reaction mixture obtained is removed until from 0.1 to 0.3 mole remains per mole of pentenoic acid ester, and any excess hydrocarbon is also removed (stage d)). Advantageously, these materials are removed by distillation, preferably under reduced pressure. In particular, the temperature of the material in the distillation vessel should not exceed 75° C., so as to avoid a decomposition of the cobalt catalyst. Depending on the alkanol chosen, part or all of the excess alkanol may be distilled off at the same time.

The pentenoic acid ester remaining in the reaction mixture is reacted with carbon monoxide and $C_1$–$C_4$-alkanol in excess (if necessary after adding an appropriate further amount of alkanol), at from 140° to 200° C. under a pressure of from 100 to 400 bar in the presence of the amount of cobalt catalyst and tertiary nitrogen base contained in the reaction mixture. Advantageously, a temperature of from 150° to 180° C. is maintained. The amount of alkanol present is advantageously from 1.5 to 4 moles per mole of pentenoic acid ester. It has also proved advantageous to add to the carbon monoxide a few percent by volume of hydrogen, for example from 1 to 4% by volume, in order to increase the rate of reaction. After releasing the pressure, the excess alkanol and the free tertiary nitrogen base are distilled from the reaction mixture obtained, but the chemically bonded tertiary nitrogen base (from 1 to 2 moles per gram atom of cobalt) is not distilled off at the same time. To avoid decomposition of the cobalt carbonyl complex, with undesired deposition of cobalt metal, it has proved advantageous to pass a slow stream of carbon monoxide, or a gas containing carbon monoxide, into the bottom of the column.

The reaction mixture which remains and which contains catalyst, butanedicarboxylic acid ester and by-products is treated, in stage (e), with an oxidizing agent in the presence of the aqueous acid solution which was separated off in stage (b).

According to the invention, the aqueous phase separated off in stage (b) is heated to 250°-350° C. under superatmospheric pressure, before being used in stage (e). As a rule, a pressure of from 40 to 300 bar, in particular the autogenous pressure, is maintained. Care must be taken that the aqueous solution contains sufficient free carboxylic acid, for example from 3 to 4% by weight, so as to avoid the deposition of metallic cobalt.

Advantageously, the heat treatment is carried out for from 0.5 to 3 hours; it can be carried out batchwise but is advantageously carried out continuously. To prevent an increase in the content of undesired by-products, not the entire amount of the aqueous phase need be treated. Preferably, only a part-stream thereof, amounting to from 5 to 50% by volume, is subjected to the heat treatment and is then combined with the remainder of the untreated aqueous solution, the combined solution being passed to stage (e).

Suitable oxidizing agents are particularly those which do not contaminate the reaction mixture, for example hydrogen peroxide or a gas containing molecular oxygen, in particular air. The oxidizing agent is used in an amount of at least 2 oxidation equivalents per mole of cobalt compound, but is advantageously employed in excess. In practice it has proved advantageous to use from 30 to 300 liters (STP) of air per kilogram of reaction mixture.

If required, suitable fatty acids may additionally be introduced into the acid aqueous solution. In any case, it is necessary to ensure that sufficient acid is present to keep the cobalt in solution. In order that the cobalt solution should not become excessively diluted, it is advantageous to recycle the aqueous cobalt-containing solution to the treatment zone and only to separate off a small part-stream, which corresponds to the amount added.

The oxidative treatment is advantageously carried out at from 80° to 160° C., especially at from 100° to 130° C. Depending on the degree of mixing, the reaction may be complete after only a few seconds and in many cases even within a fraction of a second. In order to ensure good mixing it is advisable to introduce the reaction mixture simultaneously with the oxidizing agent, in a finely dispersed form, into the aqueous acid solution.

After the treatment, the liquid phase is separated, for example by decanting, into an organic phase and an aqueous phase. Fractional distillation of the organic phase gives residual pyridine, unconverted pentenoic acid ester, which is recycled to the carbonylation, and a mixture of butanedicarboxylic acid esters (80-85% by weight of adipic acid esters, 11-15% by weight of 2-methylglutaric acid esters and 3-6% by weight of 2-ethylsuccinic acid esters).

The aqueous phase which contains cobalt salts and may contain a little free acid is advantageously extracted with a water-immiscible solvent, for example a hydrocarbon, eg. hexane, cyclohexane, pentane or a $C_4$-cut, and the organic extract is added to the reaction mixture in (e) prior to the phase separation. The aqueous phase which remains after this extraction is recycled to stage (a) as a starting solution for the preparation of cobalt carbonyl hydride.

The butanedicarboxylic acid esters prepared by the process of the invention may be used for the preparation of diols or polyesters. The adipic acid esters obtainable from the ester mixture by fractional distillation may be used for the preparation of adipic acid, nylon salt, adipodinitrile or hexanediol, ie. intermediates for synthetic fibers.

The Examples which follow illustrate the process of the invention.

COMPARATIVE EXAMPLE

A high pressure tube (stage a)) filled with 600 ml of active charcoal (from Norit, particle size 3-5 mm) is charged with 180 ml/hour of an aqueous cobalt acetate solution which contains 2.5% by weight of $Co^{2+}$. In addition, 50 liters (STP)/hour of an equimolar mixture of carbon monoxide and hydrogen are introduced. A temperature of 120° C. and a pressure of 300 bar are maintained. The solution taken off at the other end of the tube contains 0.65% by weight of $Co^{2+}$ and 1.85% by weight of cobalt as cobalt carbonyl hydride, as well as the corresponding amount of acetic acid. This solution is let down to 20 bar and then thoroughly mixed, at room temperature, with 310 ml of a $C_4$-cut which contains 43% by weight of butadiene (1.57 moles) (stage b)). After phase separation, the $C_4$-cut contains 3.7 g of cobalt in the form of cobalt carbonyl compounds. The aqueous phase separated off, which is subsequently used to remove cobalt from the reaction mixture, contains 0.65% by weight of $Co^{2+}$ and 1.3% by weight of acetic acid. This cobalt-containing $C_4$-cut is then fed to a high-pressure vessel (stage c)) of 1.9 liters capacity, and furthermore 127 ml (1.57 moles) of pyridine, 127 ml (3.14 moles) of methanol and 60 liters (STP) of carbon monoxide are added per hour. The carbonylation takes place at 130° C. and 600 bar. The product taken off at the top of the high-pressure vessel is let down, so that in addition to excess carbon monoxide excess $C_4$-hydrocarbons are separated off; the latter contain virtually no butadiene and the conversion is thus quantitative. Per hour, about 52 g of methanol and 100 g of pyridine are distilled from the material discharged (stage d)), the distillation being carried out under reduced pressure so as not to damage the catalyst. The temperature of the material in the distillation vessel is not allowed to exceed 65° C. This material, which contains 3.7 g of cobalt as carbonyl complex and 165 g (1.44 moles) of pentenoic acid ester is continuously fed, together with 117 ml (2.88 moles) of methanol and 55 liters (STP) of carbon monoxide, containing 2% by volume of hydrogen, into the bottom of a further high-pressure vessel of 1.7 liters capacity. The carbonylation is carried out at 170° C. and under a pressure of 150 bar. The excess methanol and the free pyridine are distilled from the material discharged (328 g) in a further column, whilst introducing about 50 liters (STP) of carbon monoxide per hour. The material from the bottom of the distillation column (265 g/hour) is thoroughly mixed with 200 ml/hour of the aqueous acetic acid solution obtained from the cobalt carbonyl extraction stage, at 100° C. in a tube packed with Raschig rings, whilst about 50 liters (STP) of air are being passed through (stage (e)). After separation, 200 ml of aqueous cobalt acetate solution containing 2.45% by weight of $cobalt^{2+}$ are obtained; after extraction with cyclohexane, this solution is fed to the cobalt carbonyl formation stage (a). The organic phase is separated by fractional distillation into pyridine (about 5 g), valeric acid esters (6.5 g), pentenoic acid esters (11.5 g) and dimethyl butanedicarboxylates (220 g). The latter constituent contains 181 g of dimethyl adipate.

After recycling the aqueous cobalt salt solution 25 times, the aqueous phase is found to contain, after stage (b), 0.5% by weight of cobalt as cobalt acetate, 3% by weight of acetic acid, 1.3% by weight of monomethyl adipate, 1.5% by weight of adipic acid and 1.2% by weight of nitrogen bases (N-methylpyridine, N-methyl-2-dihydropyridine and higher molecular weight N-bases).

If the recycling is continued, sparingly soluble salts separate out from the aqueous solution at 40° C.

EXAMPLE 1

The procedure followed is as described in the Comparative Example, but after 25 recyclings the aqueous phase separated off in stage (b) is heated for 2 hours at 300° C. under 100 bar autogenous pressure, before being used in stage (e). In the solution treated in this way, monomethyl adipate is decomposed quantitatively, adipic acid is 93% decomposed and the nitrogen bases are 75% decomposed. The solution thus treated now contains 0.5% by weight of cobalt as acetate, 3% by weight of acetic acid, 0.1% by weight of adipic acid and 0.3% by weight of nitrogen bases. After a further 25 recyclings, the treatment is repeated. No material is found to seperate out.

We claim:

1. In a process for the preparation of butanedicarboxylic acid esters, wherein
   (a) an aqueous cobalt salt solution is treated, at from 50° to 200° C. and under a pressure of from 50 to 500 bar, with excess carbon monoxide and hydrogen in the presence of active charcoal laden with cobalt carbonyl,
   (b) the resulting aqueous solution of cobalt carbonyl hydride is extracted with butadiene, or with a hydrocarbon mixture containing butadiene, and the aqueous phase is separated off,
   (c) the butadiene, or the butadiene/hydrocarbon mixture, containing cobalt carbonyl hydride, cobalt carbonyl and butenyl-cobalt tricarbonyl, is reacted with carbon monoxide and a $C_1$-$C_4$-alkanol in excess in the presence of from 0.5 to 2 moles, per mole of butadiene, of a tertiary nitrogen base having a $pK_a$ of from 3 to 11, at from 80° to 150° C. and under a pressure of from 300 to 2,000 bar,
   (d) the tertiary nitrogen base contained in the resulting reaction mixture is removed until its content reaches 0.1-0.3 mole per mole of pentenoic acid ester, excess hydrocarbons are also removed, the pentenoic acid ester remaining in the reaction mixture is reacted with carbon monoxide and $C_1$-$C_4$-alkanol in excess at from 140° to 200° C. and under a pressure of from 100 to 400 bar in the presence of the amounts of cobalt carbonyl and tertiary nitrogen base present in the reaction mixture, and excess alkanol and free nitrogen base are then distilled off, and
   (e) the reaction mixture which is left and which contains a cobalt catalyst, butanedicarboxylic acid ester and by-products is treated with oxidizing agents in the presence of the aqueous acid solution which has been removed in stage (b), and the mixture is separated into an organic phase, from which butanedicarboxylic acid ester is isolated by distillation, and an aqueous phase, containing cobalt salts, which is recycled to stage (a), the improvement wherein at least 5% by volume of the aqueous phase which has been separated off in stage (b) is heated at from 250° to 350° C. under superatmospheric pressure, before said aqueous phase is used in stage (e), for a period of time sufficient to decompose methyl adipate, adipic acid and nitrogen bases which have accumulated in the aqueous phase.

2. A process as claimed in claim 1, wherein autogenous pressure is used in the heat treatment of the aqueous phase separated off in stage (b).

3. A process as claimed in claim 1, wherein a part-stream of from 5 to 50% by volume of the aqueous phase obtained in (b) is heated at 250°-350° C. and is fed, together with the untreated part, to stage (e).

4. A process as claimed in claim 1 wherein said aqueous phase is heated at from 250° to 350° C. under superatmospheric pressure for 0.5 to 3 hours.

5. In a process for the preparation of butanedicarboxylic acid esters, wherein
   (a) an aqueous cobalt salt solution is treated, at from 50° to 200° C. and under a pressure of from 50 to 500 bar, with excess carbon monoxide and hydrogen in the presence of active charcoal laden with cobalt carbonyl,
   (b) the resulting aqueous solution of cobalt carbonyl hydride is extracted with butadiene, or with a hydrocarbon mixture containing butadiene, and the aqueous phase is separated off,
   (c) the butadiene, or the butadiene/hydrocarbon mixture, containing cobalt carbonyl hydride, cobalt carbonyl and butenylcobalt tricarbonyl, is reacted with carbon monoxide and a $C_1$-$C_4$-alkanol in excess in the presence of from 0.5 to 2 moles, per mole of butadiene, of a tertiary nitrogen base having a $pK_a$ of from 3 to 11, at from 80° to 150° C. and under a pressure of from 300 to 2,000 bar,
   (d) the tertiary nitrogen base contained in the resulting reaction mixture is removed until its content reaches 0.1-0.3 mole per mole of pentenoic acid ester, excess hydrocarbons are also removed, the pentenoic acid ester remaining in the reaction mixture is reacted with carbon monoxide and a $C_1$-$C_4$-alkanol in excess at from 140° to 200° C. and under a pressure of from 100 to 400 bar in the presence of the amounts of cobalt carbonyl and tertiary nitrogen base present in the reaction mixture, and excess alkanol and free nitrogen base are then distilled off, and
   (e) the reaction mixture which is left and which contains a cobalt catalyst, butanedicarboxylic acid ester and byproducts is treated with oxidizing agents in the presence of the aqueous acid solution which has been removed in stage (b), and the mixture is separated into an organic phase, from which butanedicarboxylic acid ester is isolated by distillation, and an aqueous phase, containing cobalt salts, which is recycled to stage (a), the improvement wherein at least 5% by volume of the aqueous phase which has been separated off in stage (b) is heated at from 250° to 350° C. at 40-300 bar for 0.5 to 3 hours before said aqueous phase is used in stage (e).

6. A process as claimed in claim 5, wherein 5-50% by volume of said aqueous phase is heated at 250°-350° C. and at 40-300 bar for 0.5 to 3 hours.

* * * * *